United States Patent
Hirai et al.

(10) Patent No.: US 10,955,337 B2
(45) Date of Patent: Mar. 23, 2021

(54) METHOD OF ESTIMATING OPTICAL PHYSICAL PROPERTY VALUE DISTRIBUTION, COMPUTER-READABLE RECORDING MEDIUM AND OPTICAL PHYSICAL PROPERTY VALUE DISTRIBUTION ESTIMATING APPARATUS

(71) Applicant: OLYMPUS CORPORATION, Tokyo (JP)

(72) Inventors: Nobuyuki Hirai, Hino (JP); Eiji Yasuda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 38 days.

(21) Appl. No.: 16/594,166

(22) Filed: Oct. 7, 2019

(65) Prior Publication Data
US 2020/0033262 A1    Jan. 30, 2020

Related U.S. Application Data

(63) Continuation of application No. PCT/JP2017/014869, filed on Apr. 11, 2017.

(51) Int. Cl.
*G01N 21/00* (2006.01)
*G01N 21/47* (2006.01)

(52) U.S. Cl.
CPC ..... *G01N 21/47* (2013.01); *G01N 2021/4709* (2013.01); *G01N 2201/06113* (2013.01); *G01N 2201/126* (2013.01)

(58) Field of Classification Search
CPC .......... G01J 3/44; G01N 21/65; G01N 21/64; G01N 21/47; G01N 2021/4709;
(Continued)

(56) References Cited

U.S. PATENT DOCUMENTS

2002/0026106 A1* 2/2002 Khalil ............... A61B 5/14546
                                                   600/310
2005/0002031 A1    1/2005 Kraemer et al.
(Continued)

FOREIGN PATENT DOCUMENTS

JP    2005-513491 A    5/2005
JP    2006-200943 A    8/2006
(Continued)

OTHER PUBLICATIONS

International Search Report dated May 23, 2017 issued in PCT/JP2017/014869.
(Continued)

*Primary Examiner* — Abdullahi Nur
(74) *Attorney, Agent, or Firm* — Scully, Scott, Murphy & Presser, P.C.

(57) ABSTRACT

A method of estimating an optical physical property value distribution includes: first estimating including reading a first measured value obtained by measuring isotropic backscattering light of light that is applied to a measurement subject, from a storage and estimating a first optical physical property value distribution that is an optical physical property value distribution in the measurement subject, by an inverse analysis arithmetic operation; and second estimating including reading a second measured value obtained by measuring more anisotropic backscattering light of light that is applied to the measurement subject than the backscattering light corresponding to the first measured value, from a storage and estimating a second optical physical property value distribution that is an optical physical property value distribution in the measurement subject, by an inverse analysis arithmetic operation using at least part of the first optical physical property value distribution as an initial value.

14 Claims, 12 Drawing Sheets

(58) Field of Classification Search
CPC ... G01N 2201/06113; G01N 2201/126; G01N 21/4795; A61B 10/00
See application file for complete search history.

(56) References Cited

U.S. PATENT DOCUMENTS

| | | | |
|---|---|---|---|
| 2007/0064180 A1* | 3/2007 | Hasegawa | G02F 1/133504 349/112 |
| 2013/0116553 A1 | 5/2013 | Hori et al. | |
| 2014/0135620 A1 | 5/2014 | Kudo et al. | |
| 2015/0169933 A1 | 6/2015 | Kudo et al. | |

FOREIGN PATENT DOCUMENTS

| | | |
|---|---|---|
| JP | 2013-019696 A | 1/2013 |
| JP | 2013-101060 A | 5/2013 |
| JP | 2014-027960 A | 2/2014 |
| WO | WO 02/069792 A1 | 9/2002 |

OTHER PUBLICATIONS

Abdoulaev, Gassan S. et al., "Optical tomography as a PDE-constrained optimization problem", Inverse Problems (2005), vol. 21, Institute of Physics Publishing, pp. 1507-1530, cited in spec on p. 34.

* cited by examiner

|  | $\mu a[1/mm]$ | $\mu s[1/mm]$ | g |
|---|---|---|---|
| FIRST LAYER | 0 | 0.2418 | 0.1 |
| SECOND LAYER | 0 | 3.4396 | 0.1 |

METHOD OF ESTIMATING OPTICAL PHYSICAL PROPERTY VALUE DISTRIBUTION, COMPUTER-READABLE RECORDING MEDIUM AND OPTICAL PHYSICAL PROPERTY VALUE DISTRIBUTION ESTIMATING APPARATUS

CROSS-REFERENCE TO RELATED APPLICATION

This application is a continuation of International Application No. PCT/JP2017/014869, filed on Apr. 11, 2017, the entire contents of which are incorporated herein by reference.

BACKGROUND

1. Technical Field

The present disclosure relates to a method of estimating an optical physical property value distribution, a computer-readable recording medium, and an optical physical property value distribution estimating apparatus.

2. Related Art

A method using reflectance diffuse optical tomography has been known as a method of non-invasively estimating a distribution of optical physical property values in living tissue (for example, refer to Japanese National Publication of International Patent Application No. 2005-513491, International Publication Pamphlet No. WO 2002/069792 and Japanese Laid-open Patent Publication No. 2006-200943). In this method, first of all, light is applied to a measurement subject and backscattering light from the measurement subject is received, thereby acquiring measured values of the backscattering light.

An optical physical property value distribution in the measurement subject is speculated on, numerical value calculation is performed using a light propagation model, and backscattering light caused by the measurement subject is calculated as a predicted value. Specifically, a subject measurement model is sectioned into meshes (or voxels) and a scattering coefficient and an absorption coefficient are set as parameters for each of the meshes and propagation of light in the measurement subject is calculated by an optical transport equation or an optical diffusion equation. A measured value and the predicted value are compared with each other and it is determined whether a degree of concordance is at or above a given value. When the degree of concordance is under the given value, an optical physical property value distribution in the measurement subject is speculated on again and a predicted value is calculated, and this calculation is repeated until the degree of concordance is at or above the given value. The repeated calculation is also referred to as inverse analysis arithmetic operation. Setting an error function from the difference between the measured value and the predicted value enables evaluation of the degree of concordance. Speculating on an optical physical property value distribution in the measurement subject again such that the error function decreases enables reduction in difference between the measured value and the predicted value. Known various optimization algorithms are applicable to the inverse analysis arithmetic operation mentioned above.

Japanese National Publication of International Patent Application No. 2005-513491 discloses that applying illumination obliquely to a measurement subject and receiving backscattering light from the measurement subject in an oblique direction opposed to the illuminating direction enables accurate estimation of an optical physical property value distribution in a shallow layer of the measurement subject.

International Publication Pamphlet No. WO 2002/069792 discloses that measurement in a plurality of illuminating directions and a plurality of light receiving directions enables more accurate estimation of an optical physical property value distribution in a shallow layer of the measurement subject.

Japanese Laid-open Patent Publication No. 2006-200943 discloses that backscattering light of light having reached a deep layer of a living body scatters for a large number of times and thus is isotropic. In other words, the light intensity of backscattering light of light having reached a deep layer of a living body has low dependence on angle. On the other hand, it is disclosed that there is a tendency that, the deeper a layer light reaches is, the larger a phase shift that is TOF (Time Of Flight) information of the backscattering light from the measurement subject is and thus it is possible to accurately estimate an optical physical property value distribution in a deep layer of the measurement subject using the TOF information.

SUMMARY

In some embodiments, provided is a method of estimating an optical physical property value distribution that is performed by an optical physical property value distribution estimating apparatus configured to estimate an optical physical property value distribution in a measurement subject. The method includes: first estimating including reading a first measured value obtained by measuring isotropic backscattering light of light that is applied to the measurement subject, from a storage and estimating a first optical physical property value distribution that is an optical physical property value distribution in the measurement subject, by an inverse analysis arithmetic operation; and second estimating including reading a second measured value obtained by measuring more anisotropic backscattering light of light that is applied to the measurement subject than the backscattering light corresponding to the first measured value, from a storage and estimating a second optical physical property value distribution that is an optical physical property value distribution in the measurement subject, by an inverse analysis arithmetic operation using at least part of the first optical physical property value distribution as an initial value.

In some embodiments, provided is a method of estimating an optical physical property value distribution that is performed by an optical physical property value distribution estimating apparatus configured to estimate an optical physical property value distribution in a measurement subject. The method includes: first estimating including reading a first measured value obtained by measuring backscattering light of light that is applied to the measurement subject, from a storage and estimating a first optical physical property value distribution that is an optical physical property value distribution in a first area containing an area on which it is supposed that an optical energy loss in the measurement subject is large, by an inverse analysis arithmetic operation; and second estimating including reading a second measured value obtained by measuring backscattering light of light that is applied to the measurement subject, from a storage and estimating a second optical physical property value distribution that is an optical physical property value distribution in a second area on which it is supposed that a loss of optical energy is smaller than the optical energy loss in the first area in the measurement subject, by an inverse analysis arithmetic operation using at least part of the first optical physical property value distribution as an initial value.

In some embodiments, provided is a method of estimating an optical physical property value distribution that is performed by an optical physical property value distribution estimating apparatus configured to estimate an optical physical property value distribution in a measurement subject. The method includes: first estimating including reading a first measured value obtained by measuring backscattering light of light that is applied to a first area in the measurement subject, from a storage and estimating a first optical physical property value distribution that is an optical physical property value distribution in the measurement subject, by an inverse analysis arithmetic operation; and second estimating including reading a second measured value obtained by measuring backscattering light of light that is applied to a second area contained in the first area from a storage and estimating a second optical physical property value distribution that is an optical physical property value distribution of a layer shallower than a layer corresponding to the first physical property value distribution in the measurement subject, by an inverse analysis arithmetic operation using at least part of the first optical physical property value distribution as an initial value.

In some embodiments, provided is a non-transitory computer-readable recording medium with an executable program stored thereon. The program causes an optical physical property value distribution estimating apparatus configured to estimate an optical physical property value distribution in a measurement subject to execute: first estimating including reading a first measured value obtained by measuring isotropic backscattering light of light that is applied to the measurement subject, from a storage and estimating a first optical physical property value distribution that is an optical physical property value distribution in the measurement subject, by an inverse analysis arithmetic operation; and second estimating including reading a second measured value obtained by measuring more anisotropic backscattering light of light that is applied to the measurement subject than the backscattering light corresponding to the first measured value, from a storage and estimating a second optical physical property value distribution that is an optical physical property value distribution of a layer shallower than a layer corresponding to the first optical physical property value distribution in the measurement subject, by an inverse analysis arithmetic operation using at least part of the first optical physical property value distribution as an initial value.

In some embodiments, provided is an optical physical property value distribution estimating apparatus configured to estimate an optical physical property value distribution in a measurement subject. The apparatus includes an inverse analysis arithmetic circuit configured to read a first measured value obtained by measuring isotropic backscattering light of light that is applied to the measurement subject, from a storage and estimate a first optical physical property value distribution that is an optical physical property value distribution in the measurement subject, by an inverse analysis arithmetic operation, and read a second measured value obtained by measuring more anisotropic backscattering light of light that is applied to the measurement subject than the backscattering light corresponding to the first measured value, from a storage and estimate a second optical physical property value distribution that is an optical physical property value distribution of a layer shallower than a layer corresponding to the first optical physical property value distribution in the measurement subject, by an inverse analysis arithmetic operation using at least part of the first optical physical property value distribution as an initial value.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
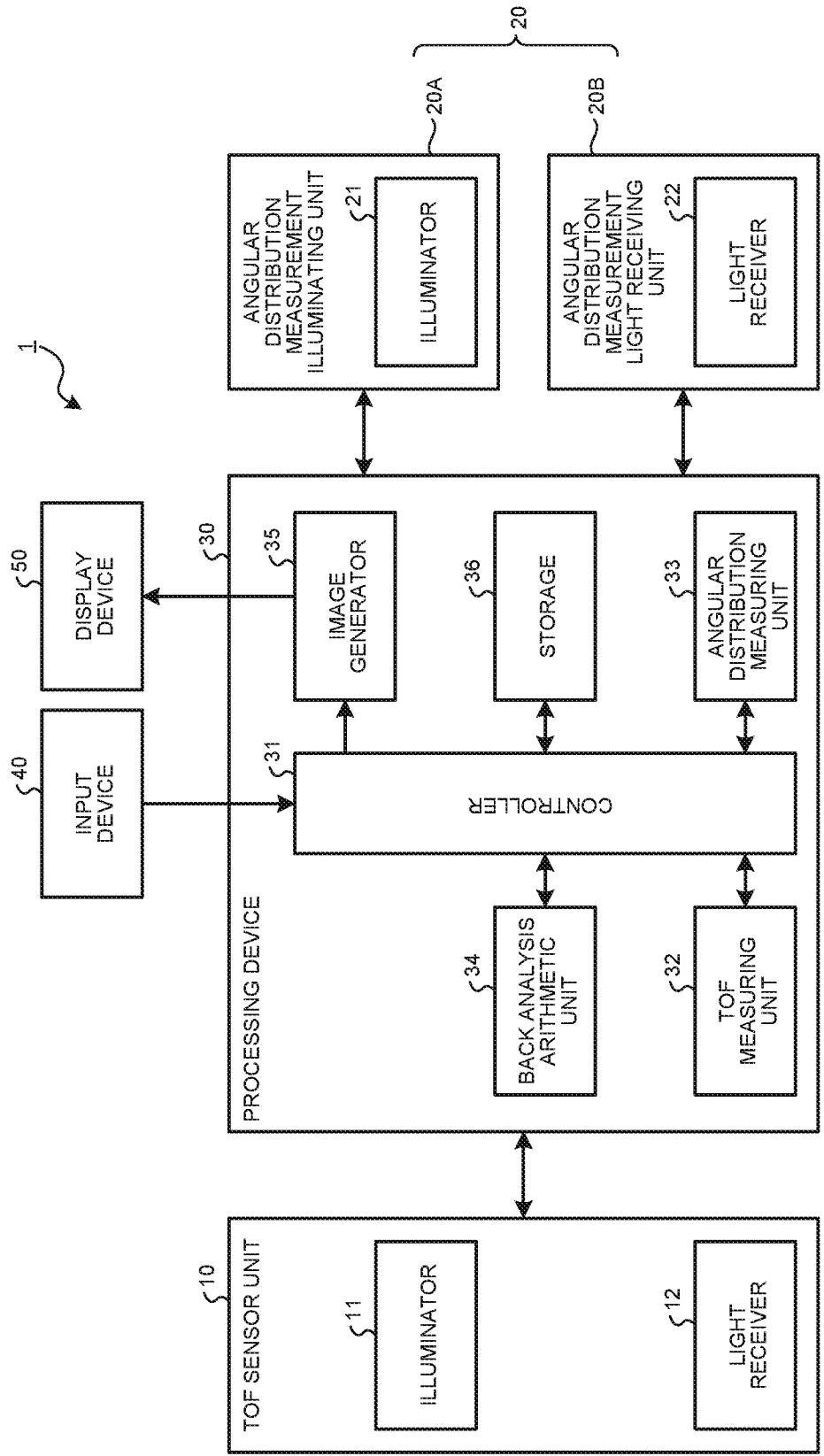
FIG. 1 is a block diagram illustrating a configuration of an optical physical property value distribution estimating apparatus according to a first embodiment.

Embodiments of a method of estimating an optical physical property value distribution, a program for estimating an optical physical property value distribution, and an optical physical property value distribution estimating apparatus will be described. The embodiments do not limit the disclosure. The following embodiments will be described by exemplifying a method of estimating an optical physical property value distribution to estimate an optical physical property value distribution using TOF information and a light intensity angular distribution as a measured value. The disclosure is also applicable to a method of estimating an optical physical property value distribution using another measured value.

As for illustration in the drawings, like or corresponding components are denoted with like reference numerals as appropriate. It should be noted that the drawings are schematic and thus the relationship in size among components, the ratio among components, etc., can differ from actual ones. The drawings may also contain parts whose mutual relationship in size or ratio differ among the drawings.

FIRST EMBODIMENT

FIG. 1 is a block diagram illustrating a configuration of an optical physical property value distribution estimating apparatus according to a first embodiment. An optical physical property value distribution estimating apparatus 1 according to the first embodiment is an apparatus that estimates an optical physical property value distribution in a measurement subject. As illustrated in FIG. 1, the optical physical property value distribution estimating apparatus 1 includes a TOF sensor unit 10 that applies light whose intensity is modulated periodically to the measurement subject and receives backscattering light in the measurement subject; an angular distribution measuring device 20 that applies light to the measurement subject such that the angle is changeable and receives backscattering light in the measurement subject such that the angle is changeable; a processing device 30 that processes signals that are acquired by the TOF sensor unit 10 and the angular distribution measuring device 20; an input device 40 that receives various inputs made by a user; and a display device 50 that displays an image that is generated by the processing device 30.

The TOF sensor unit 10 includes an illuminator 11 that applies light whose light intensity is modulated periodically to the measurement subject; and a light receiver that receives backscattering light of the applied light in the measurement subject.

Figure 2:
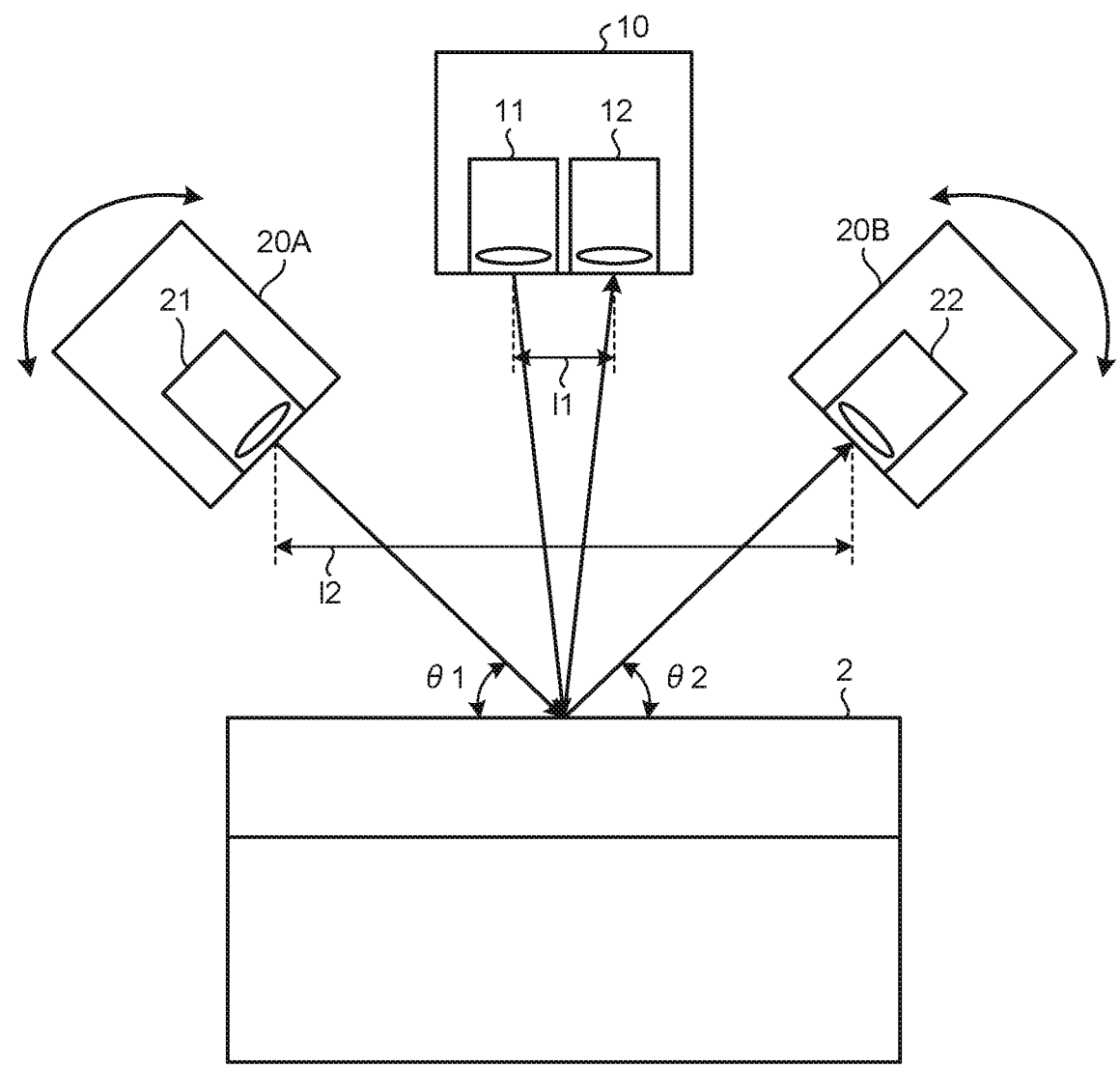
FIG. 2 is a diagram illustrating that a TOF sensor unit, an angular distribution measurement illuminating unit and an angular distribution measurement light receiving unit that are illustrated in FIG. 1 are arranged with respect to a measurement subject.

FIG. 2 is a diagram illustrating that the TOF sensor unit, the angular distribution measurement illuminating unit, and the angular distribution measurement light receiving unit that are illustrated in FIG. 1 are arranged with respect to the measurement subject. The TOF sensor unit 10 applies light to the surface of a measurement subject 2 approximately orthogonally and receives backscattering light in a direction approximately orthogonal to the surface of the measurement subject 2. In FIG. 2, for convenience of illustration, the angle at which light is applied and the angle at which the light is received deviate from a direction orthogonal to the surface of the measurement subject 2; however, in practice, the TOF sensor unit 10 is arranged such that the angles are approximately orthogonal to the surface of the measurement subject 2.

The illuminator 11 includes, for example, a light source that is a light emitting diode (LED) and applies light of a wavelength of 850 nm. The illuminator 11 applies light whose light intensity is modulated to a sine wave of 30 MHz according to control performed by the processing device 30. Note that modulation of intensity of light applied from the light source may lead to pulsed light or a square wave. The wavelength of light applied from the illuminator 11 is not particularly limited, and the wavelength may be variable or light with a wide wavelength band may be used. The light applied from the light source may be applied to the measurement subject 2 via a diffusing lens, a condenser lens, an optical fiber, etc.

A light receiver 12 includes a photodetector that is a CMOS (Complementary Metal Oxide Semiconductor) TOF sensor chip. The photodetector converts the received light to an electric signal by photoelectric conversion. Note that the photodetector may be a CCD (Charge Coupled Devices) TOF sensor chip. The photodetector may receive the backscattering light in the measurement subject 2 via a condenser lens, a wavelength filter that transmits only light of a given wavelength, etc.

The angular distribution measuring device 20 includes an angular distribution measurement illuminating unit 20A and an angular distribution measurement light receiving unit 20B. The angular distribution measurement illuminating unit 20A includes an illuminator 21 and applies light to the measurement subject 2 at a variable angle. The angular distribution measurement light receiving unit 20B includes a light receiver 22 and receives the backscattering light of the applied light in the measurement subject 2 at a variable angle.

The illuminator 21 has, for example, a light source that is an LED and applies light of a wavelength of 850 nm. The wavelength of light that is applied from the illuminator 21 is not particularly limited and may be variable or light having a wide wavelength band may be used. The light applied from the light source may be applied to the measurement subject 2 via a diffusing lens, a condenser lens, an optical fiber, etc. As the illuminator 11 does, the illuminator 21 may apply light whose light intensity is modulated periodically.

The light receiver 22 may have the same configuration as that of the light receiver 12 or may differ from the light receiver 12 in configuration and sensitivity.

The processing device 30 includes a controller 31, a TOF measuring unit 32, an angular distribution measuring unit 33, an inverse analysis arithmetic unit 34, an image generator 35, and a storage 36.

The controller 31 is achieved using a central processing unit (CPU), or the like. The controller 31 controls processing operations of each unit of the processing device 30. The controller 31 transfers instruction information and data to each component of the processing device 30, thereby controlling operations of the processing device 30. The controller 31 performs control such that operations of the illuminator 11 and the light receiver 12 and operations of the illuminator 21 and the light receiver 22 synchronize with each other.

The TOF measuring unit 32 measures, as a first measured value obtained by measuring isotropic backscattering light of the light applied to the measurement subject 2, TOF information that is information on a phase shifts in intensity modulation each between the light applied from the illuminator 11 and the light received by the light receiver 12. Specifically, a phase of light that is applied by the illuminator 11 is received from the controller 31, a phase of received light is received from the light receiver 12, and a phase shift $\varphi$ is calculated by comparing the acquired phases. The calculated TOF information is stored in the storage 36. The first measured value may be values measured using at least any one of a photoacoustic phenomenon and a cross Nicol method.

Figure 3:
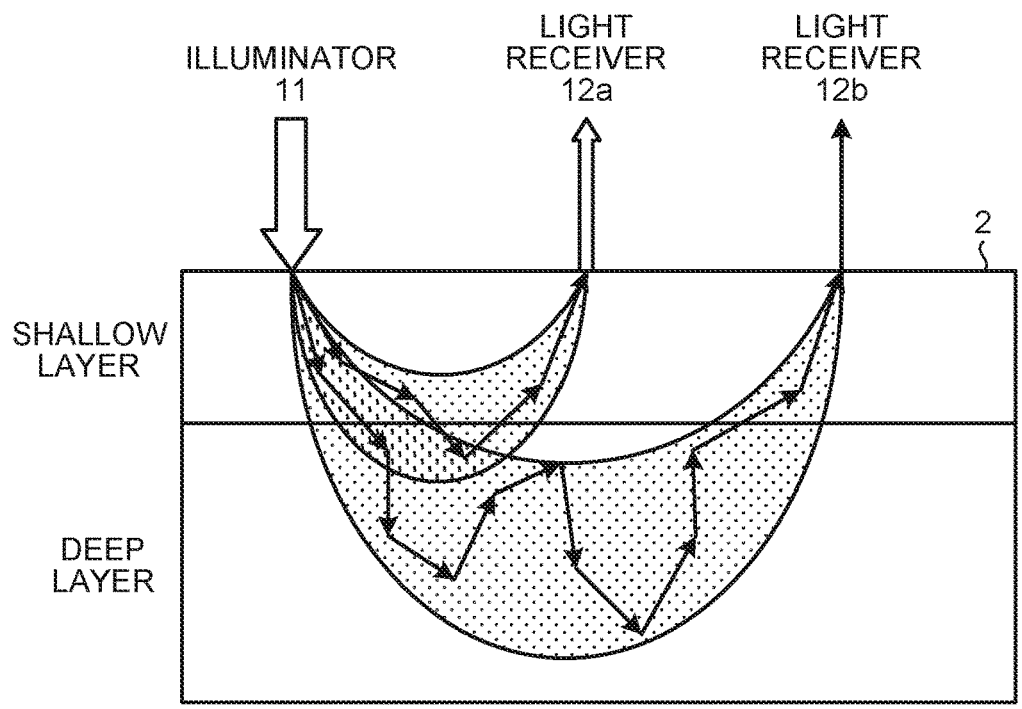
FIG. 3 is a diagram illustrating that the TOF sensor unit illustrated in FIG. 2 measures a first measured value.

FIG. 3 is a diagram illustrating that the TOF sensor unit illustrated in FIG. 2 measures the first measured value. As illustrated in FIG. 3, in the TOF sensor unit 10, the illuminator 11 applies light orthogonally to the surface of the measurement subject 2 and a light receiver 12a and a light receiver 12b receive backscattering light of the measurement subject 2 in a direction orthogonal to the surface of the measurement subject 2. The backscattering light from a shallow layer of the measurement subject 2 that is detected by the light receiver 12a positioned near the illuminator 11 is anisotropic backscattering light with a lot of components in a direction orthogonal to the surface of the measurement subject 2. On the other hand, the backscattering light from a deep layer of the measurement subject 2 that is detected by the light receiver 12b arranged in a position more distant from the illuminator 11 than that of the light receiver 12a is isotropic backscattering light whose components in respective direction are equalized. The TOF sensor unit 10 detects information on the measurement subject 2 by the phase shift φ and thus is suitable for detection of information from a deep layer. The TOF sensor unit 10 may be configured to include a plurality of light receivers corresponding to the light receiver 12a and the light receiver 12b or may be configured to move a single light receiver to positions corresponding to the light receiver 12a and the light receiver 12b and perform measurement.

The angular distribution measuring unit 33 measures, as a second measured value obtained by measuring more anisotropic backscattering light of light that is applied to the measurement subject 2 than the backscattering light corresponding to the first measured value, an angular distribution of light intensity of backscattering light corresponding to light that is applied from the illuminator 21. Specifically, under the control of the controller 31, an angle θ2 at which the light receiver 22 receives light is changed with respect to light that is applied at an angle θ1 from the illuminator 21 and then a light intensity is detected. Furthermore, the angle θ1 of illumination from the illuminator 21 is changed, the angle θ2 at which the light receiver 22 receives light is changed similarly, and measurement is repeated. The measured light intensity angular distribution is stored in the storage 36. Only any one of the angle θ1 and the angle θ2 may be changed. Furthermore, any one of the angle θ1 and the angle θ2 may be an acute angle (larger than 0° and smaller than 90°) and the other angle may be 90°. The second measured value may be values that are measured using at least any one of OCT (Optical Coherence Tomography) an open Nicol method. The cross Nicol enables measurement of light of multiple scattering in the measurement subject 2, and the open Nicol enables measurement of light of multiple scattering in the measurement subject 2 and light that reflects or scatters (single scattering) on the surface of the measurement subject 2. Accordingly, the second measured value may be a value measured using both the cross Nicol method and the open Nichol method.

Figure 4:
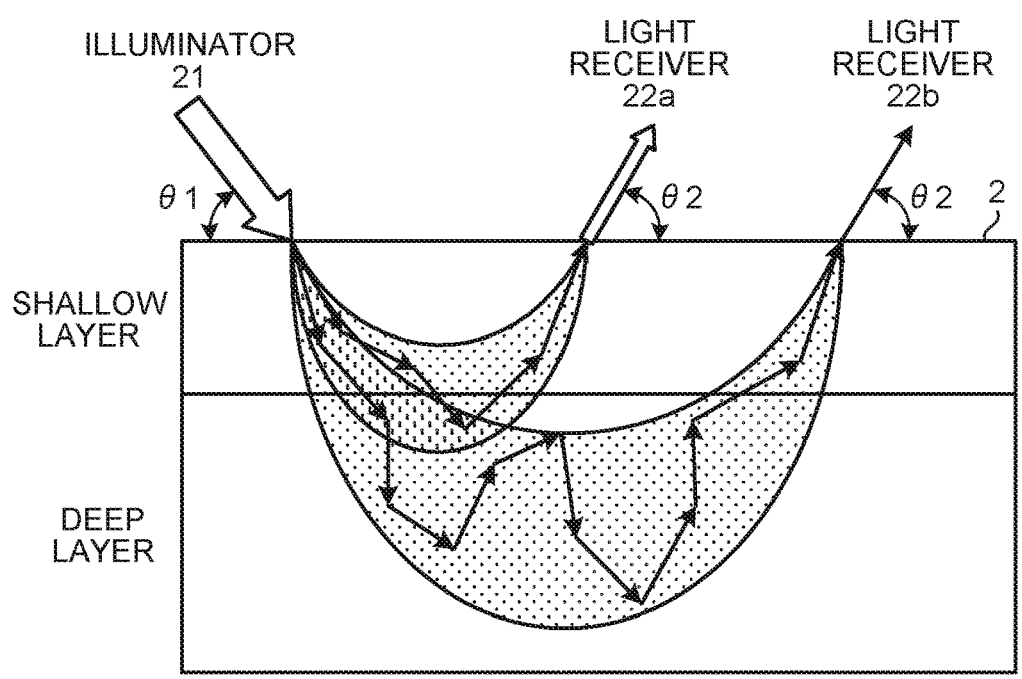
FIG. 4 is a diagram illustrating that the angular distribution measuring device illustrated in FIG. 2 measures a second measured value.

FIG. 4 is a diagram illustrating that the angular distribution measuring device illustrated in FIG. 2 measures the second measured value. As illustrated in FIG. 4, the angular distribution measuring device 20 applies light to the surface of the measurement subject 2 at an angle θ1 and a light receiver 22a and a light receiver 22b receive backscattering light from the measurement subject 2 at angles θ2 with respect to the surface of the measurement subject 2. The backscattering light from the shallow layer of the measurement subject 2 that is detected by the light receiver 22a positioned near the illuminator 21 is anisotropic backscattering light with a lot of components in a specific direction containing information on a light propagation path of the back scattering light and a light path length thereof, and the light intensity of the backscattering light differs depending on the angle. On the other hand, the back scattering light from the deep layer of the measurement subject 2 that is detected by the light receiver 22b arranged in a position more distant from the illuminator 21 than the light receiver 22a is isotropic backscattering light whose components in respective directions are equalized and the light intensity of the backscattering light is equal at any angle. Accordingly, the angular distribution measuring device 20 is able to accurately obtain information on the shallow layer but is not suitable for acquisition of information on the deep layer.

The inverse analysis arithmetic unit 34 reads the TOF information that is measured by the TOF measuring unit 32 from the storage 36 and estimates a first optical physical property value distribution that is an optical physical property value distribution in the measurement subject 2 by an inverse analysis arithmetic operation. The inverse analysis arithmetic unit 34 further reads the light intensity angular distribution of backscattering light that is measured by the angular distribution measuring unit 33 from the storage 36 and estimates a second optical physical property value distribution that is an optical physical property value distribution of the shallower layer than that of the first optical physical property value distribution in the measurement subject 2 by an inverse analysis arithmetic operation using at least part of the first optical physical property value distribution as an initial value. The inverse analysis arithmetic unit 34 may cause a CPU that is provided in the optical physical property value distribution estimating apparatus 1, or the like, to perform the arithmetic operation. Alternatively, the inverse analysis arithmetic unit 34 may cause a CPU that is provided outside the optical physical property value distribution estimating apparatus 1, or the like, to perform the inverse analysis operation.

The first optical physical property value distribution and the second optical physical property value distribution are, for example, scattering coefficient distributions. The first optical physical property value distribution and the second optical physical property value distribution may be absorbing confident distributions, scattering anisotropy distributions, or the like.

Light diffuses in a process of propagation of light in living tissue (a scattering absorber) and accordingly optical energy gets lost because of the scattering and absorption. When light propagation is anisotropic (non-diffusive), an effective light propagation distance in the living tissue is relatively short and thus an optical energy loss is relatively small. On the other hand, when light propagation is isotropic (diffusive), an effective light propagation distance in the living tissue is relatively long and thus an optical energy loss is relatively large. Thus, a first optical physical property value distribution that is an optical physical property value distribution in a first area (the shallow layer and the deep layer) containing an area (the deep layer) on which it is supposed that an optical energy loss in the measurement subject 2 is large is estimated using the first measured value that is acquired by the TOF measuring unit 32 and a second optical physical property value distribution that is an optical physical property value distribution in a second area (the shallow layer) where it is supposed that an optical energy loss is smaller than that in the first area in the measurement subject 2 is estimated using the second measured value that is acquired by the angular distribution measuring unit 33.

The image generator 35 generates an image signal based on the optical properties that are calculated by the inverse analysis arithmetic unit 34 by performing an arithmetic operation and outputs the image signal. Specifically, the image generator 35 generates an image signal obtained by changing the density, color, contrast, etc., according to the value of optical properties per pixel that is calculated by the inverse analysis arithmetic unit 34 by performing an arithmetic operation. The image generator 35 may generate an image signal obtained by superimposing an image obtained by changing the color, etc., according to the value of optical properties on 2D and 3D images captured by various cameras and an ultrasound image, etc. The image generator 35 may generate an image in which the inverse analysis arithmetic unit 34 represents optical properties by numerical values or a graph by an arithmetic operation.

The storage 36 stores various programs for causing the optical physical property value distribution estimating apparatus 1 and data containing various parameters necessary for operations of the optical physical property value distribution estimating apparatus 1, etc. The storage 36 stores the first measured value based on the result of measuring by the TOF measuring unit 32 and stores the second measured value based on the result of measuring by the angular distribution measuring unit 33.

The storage 36 stores various programs including an operation program for executing an operation method for the optical physical property value distribution estimating apparatus 1. The operation program is also recordable in a computer-readable recording medium, such as a hard disk, a flash memory, a CD-ROM, a DVD-ROM or a flexible disk, and is widely distributable. By downloading the above-described various programs via a communication network, it is possible to acquire the various programs. The communication network herein is achieved with, for example, an existing public network, a local area network (LAN), a wide area network (WAN), or the like, and it does not matter whether the communication network is wired or wireless.

The storage 36 having the above-described configuration is achieved using a read only memory (ROM) in which the various programs are installed in advance, a random access memory (RAM) that stores arithmetic parameters and data for each set of processing, or the like.

The input device 40 is achieved using operational devices, such as a mouse, a keyboard, a touch panel, etc. The input device 40 receives input of various types of instruction information of the optical physical property value distribution estimating apparatus 1 and outputs the various types of instruction information to the controller 31.

The display device 50 is configured using a display using liquid crystals or organic electro luminescence (EL). The display device 50 displays an image based on the image signal that is output by the image generator 35.

Figure 5:
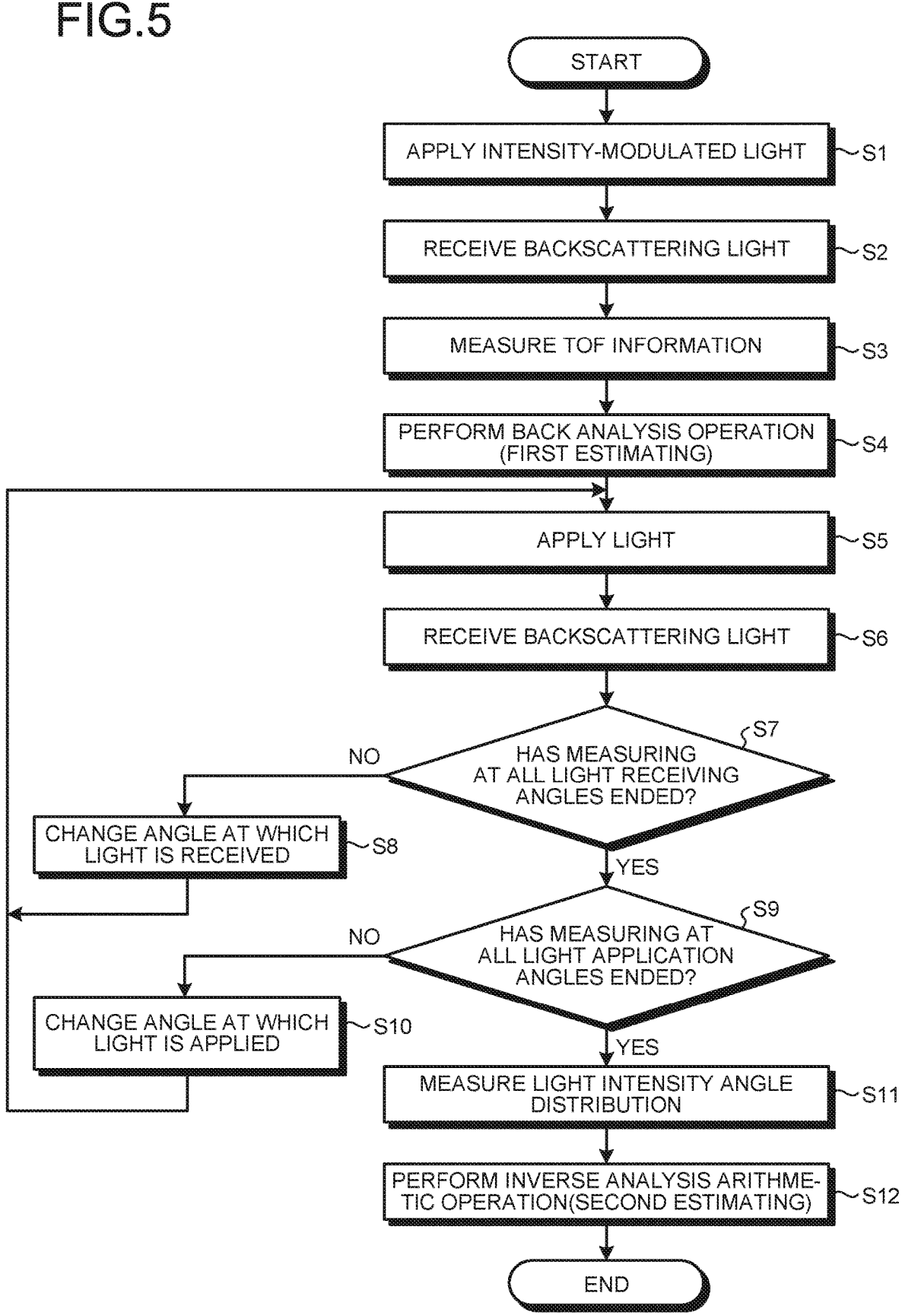
FIG. 5 is a flowchart illustrating operations of the optical physical property value estimating apparatus to perform measurement on the measurement subject.

Operations of the optical physical property value distribution estimating apparatus 1 will be described. FIG. 5 is a flowchart illustrating operations of the optical physical property value distribution estimating apparatus illustrated in FIG. 1 to perform measurement on the measurement subject. As illustrated in FIG. 5, first of all, intensity-modulated light is applied from the illuminator 11 of the TOF sensor unit 10 to the measurement subject 2 (step S1). The light receiver 12 of the TOF sensor unit 10 then receives backscattering light from the measurement subject 2 (step S2).

The TOF measuring unit 32 of the processing device 30 measures TOF information that is information on a phase shift φ of intensity modulation between the light applied from the illuminator 11 and the light received by the light receiver 12 (step S3).

The inverse analysis arithmetic unit 34 estimates a first optical physical property value distribution in the measurement subject 2 by an inverse analysis arithmetic operation based on the TOF information (step S4: first estimating).

Light is then applied from the illuminator 21 of the angular distribution measurement illuminating unit 20A to the measurement subject 2 at a given light application angle (step S5). The light receiver 22 of the angular distribution measurement light receiving unit 20B then receives backscattering light from the measurement subject 2 at a given light receiving angle (step S6).

The controller 31 then determines whether measurement at all light receiving angles has ended (step S7). When the controller 31 determines that measurement at all the light receiving angles has not ended (NO at step S7), the angle at which the light receiver 22 receives light is changed under the control of the controller 31 (step S8) and measuring at steps S5 and S6 is repeatedly performed.

On the other hand, when the controller 31 determines that measuring at all the light receiving angles has ended (YES at step S7), the controller 31 determines whether measuring at all light application angles has ended (step S9). When the controller 31 determines that measuring at all the light application angles has not ended (NO at step S9), the angle at which the illuminator 21 applies light is changed under the control of the controller 31 (step S10) and measuring at steps S5 to S7 is performed repeatedly.

On the other hand, when the controller 31 determines that measuring at all the light application angles has ended (YES at step S9), the angular distribution measuring unit 33 of the processing device 30 measures an angular distribution of light intensities of backscattering light corresponding to the light applied from the illuminator 21 (step S11).

Based on the light intensity angular distribution of backscattering light that is measured by the angular distribution measuring unit 33, the inverse analysis arithmetic unit 34 estimates a second optical physical property value distribution that is an optical physical value distribution in a shallower layer than that of the first optical physical value distribution in the measurement subject 2 by an inverse analysis arithmetic operation using the first optical physical property values as an initial value (step S12: second estimating).

In the above-described flowchart, the example where measuring at steps S1 to S3 is performed, the arithmetic operation at step S4 is performed, measuring at steps S5 to S11 is performed, and the arithmetic operation at step S12 is performed has been described; however, embodiments are not limited thereto. For example, measuring at steps S1 to S3 and measuring at steps S5 to S11 may be performed sequentially or in parallel and then the arithmetic operation at step S4 and the arithmetic operation at step S12 may be performed.

As described above, first of all, the optical physical property value distribution estimating apparatus 1 estimates the first optical physical property value distribution in the measurement subject 2 by performing the inverse analysis arithmetic operation based on the TOF information. Based on the optical physical property value distribution, the inverse analysis arithmetic unit 34 then estimates the second optical physical property value distribution that is optical physical property values in the shallow layer by performing the inverse analysis arithmetic operation using the first optical physical property value distribution as the initial value.

Why optical physical property values are estimated using the isotropic backscattering light from the deep layer (backscattering light in the direction orthogonal to the measurement subject 2) will be described. It is assumable that components propagated by light in the shallow layer consist of components that are directly propagated by light from the illuminating light and components that are indirectly propagated by re-illuminating the shallow layer with the return light resulting from backscattering of the light having reached the deep layer. For this reason, in order to accurately estimate optical physical property values in the shallow layer area, it is necessary to roughly know the intensity of the backscattering light from the deep layer area.

When scattering or absorption in the deep layer area is relatively greater than that in the shallow layer area, or when the deep layer area is thicker than the shallow layer area (such as digestive organ tissue), it is assumable that the components propagated by light in the deep layer are more affected by the optical physical value property value distribution in the deep layer area than in the shallow layer area.

Figure 6:
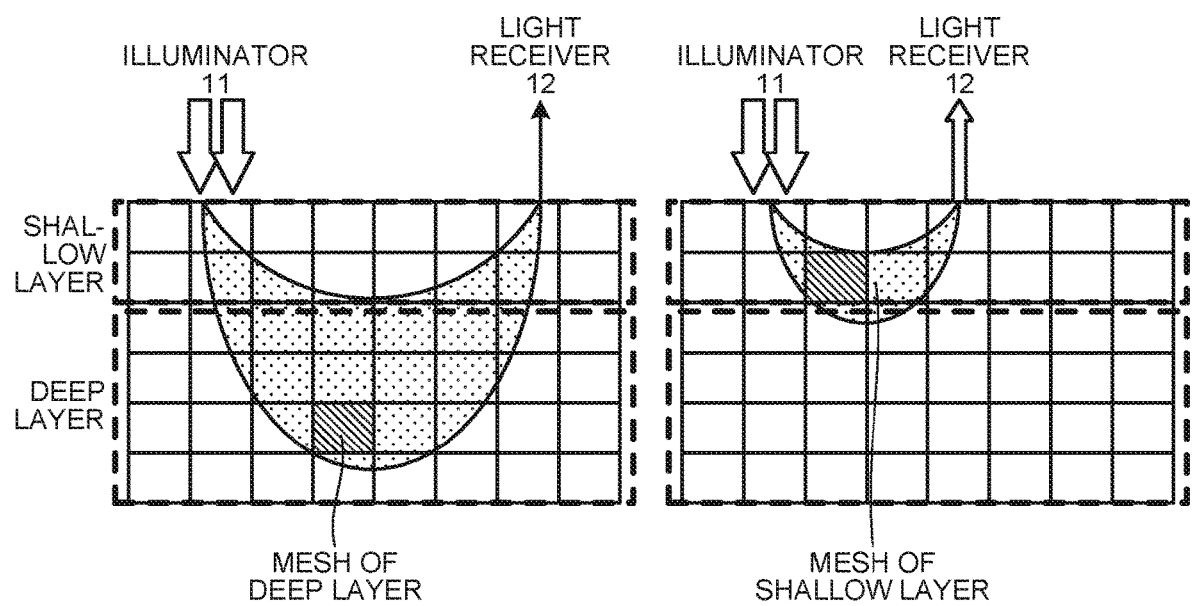
FIG. 6 is a diagram illustrating propagation of light in a deep layer and a shallow layer.

FIG. 6 is a diagram illustrating propagation of light in the deep layer and the shallow layer. As illustrated in FIG. 6, in general, a deep layer area has a larger volume (area of the cross section in FIG. 6) than that of a shallow layer area in a living body. For this reason, the deep layer area has a greater effect on the light intensity of backscattering light received by the light receiver 12 than that of the shallow layer area in the whole area. In other words, the deep layer area largely contributes to an error function in a process of performing an estimation calculation. On the other hand, because the optical energy reduces in the process in which the light reaches the deep layer, the deep layer has a smaller effect than that of the deep layer on the light intensity of backscattering light that is received by the light receiver 12. In other words, the shallow layer is more sensitive than the deep layer to change in light intensity of backscattering light corresponding to change in physical property value of each mesh. In other words, in the process of performing estimation calculation, the optical physical property value parameter of each mesh of the shallow layer changes rapidly relatively and the optical physical property value parameter of each mesh of the deep layer changes sluggishly. Accordingly, when the optical physical property value parameters are estimated simultaneously (or the optical physical property value parameter of the shallow layer is estimated first), only the physical property value parameter of the shallow layer changes and estimation on the deep layer cannot be performed and furthermore the accuracy of calculating an amount of backscattering light from the deep layer to the shallow layer direction deteriorates, which lowers the accuracy of estimation on the shallow layer.

For this reason, it is preferable that the optical physical property values of the deep layer with sluggish change in physical property value. Accordingly, in the optical physical property value distribution estimating apparatus 1, first of all, the first optical physical property values in a wide area from a shallow layer to a deep layer are estimated according to the TOF information.

Why the TOF information is used to estimate the optical physical property values of the deep layer and why the light intensity angular distribution is used to estimate the optical physical property values of the shallow area will be described. The number of times of scattering of the backscattering light having returned to the surface layer from the shallow layer area is small and thus information on the light propagation path and the light path length remains in the information on the light intensity angular distribution. On the other hand, the number of times of scattering of the backscattering light having reached the deep layer area and having returned to the surface layer is large and thus the light intensity angular distribution is isotropic and the information on the light propagation path and the light path length is lost. On the other hand, the information on the light propagation path and the light path length remains in the TOF information. Thus, it is preferable that the TOF information be used to estimate the optical physical property value distribution in the deep layer area and the angular distribution information on the backscattering light be used to estimate the optical physical property value distribution in the shallow layer area. Note that known various methods may be used to detect backscattering light from the shallow layer area and the deep layer area.

EXAMPLE

Figure 7:
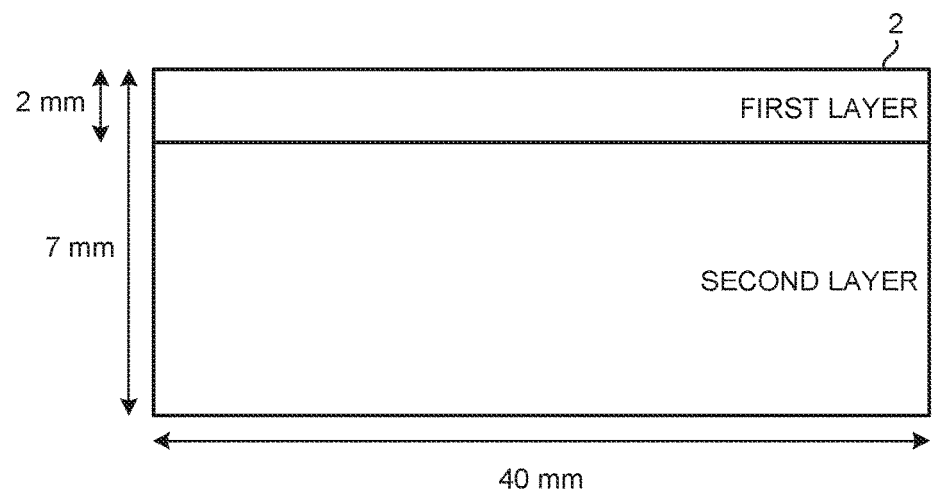
FIG. 7 is a diagram illustrating a measurement subject on which the optical physical property value distribution estimating apparats according to an example performs measurement.

FIG. 7 is a diagram illustrating a measurement subject on which an optical physical property value distribution estimating apparatus according to Example performs measurement. As illustrated in FIG. 7, in Example, using the optical physical property value distribution estimating apparatus 1, an optical physical property value distribution in the measurement subject 2 whose optical physical property values differ between a first layer and a second layer is measured. The first layer has a thickness of 2 mm and the measurement subject 2 has an overall thickness of 7 mm and a width of 40 mm.

Figures 8, 9:
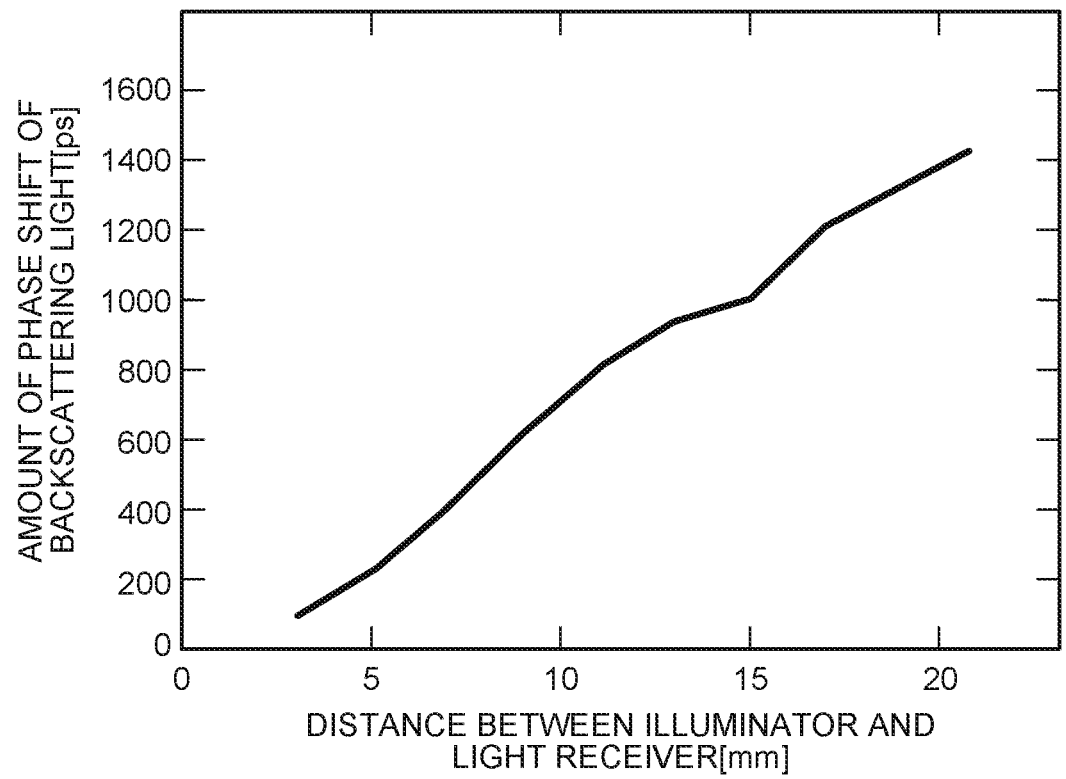
FIG. 8 is a table representing optical physical property values of the measurement subject illustrated in FIG. 7.
FIG. 9 is a graph representing a result of measurement performed by the TOF measuring unit.

FIG. 8 is a table representing optical physical property values of the measurement subject illustrated in FIG. 7. As represented in FIG. 8, the first layer and the second layer are equal in absorption coefficient μa [1/mm] and scattering anisotropy g but differ in scattering coefficient ps [1/mm]. In Example, a scattering coefficient distribution is estimated using a scatterer without absorption (μa=0) as the measurement subject 2. Alternatively, in the same manner, it is possible to estimate a scattering coefficient distribution and an absorption coefficient distribution using a scatterer with absorption as the measurement subject.

FIG. 9 is a graph representing a result of measurement by the TOF measuring unit. As illustrated in FIG. 9, increasing a distance 11 [mm] between the illuminator 11 and the light receiver 12 (refer to FIG. 2) increases an amount [ps] of a phase shift φ of intensity modulation between light applied from the illuminator 11 and light received by the light receiver 12. Note that the phase shift φ may be measured by another known technique.

Figure 10:
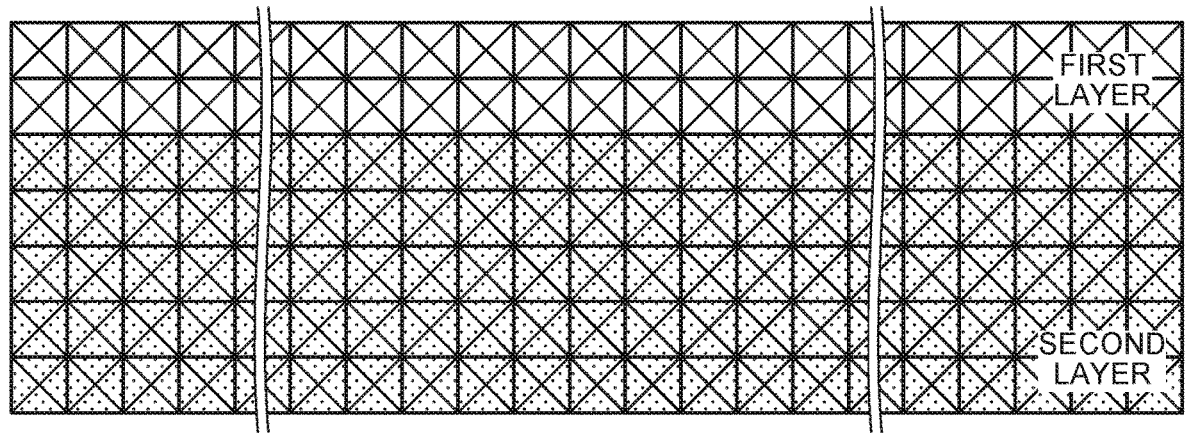
FIG. 10 is a diagram illustrating that the measurement subject illustrated in FIG. 7 is divided into meshes.
Figure 11:
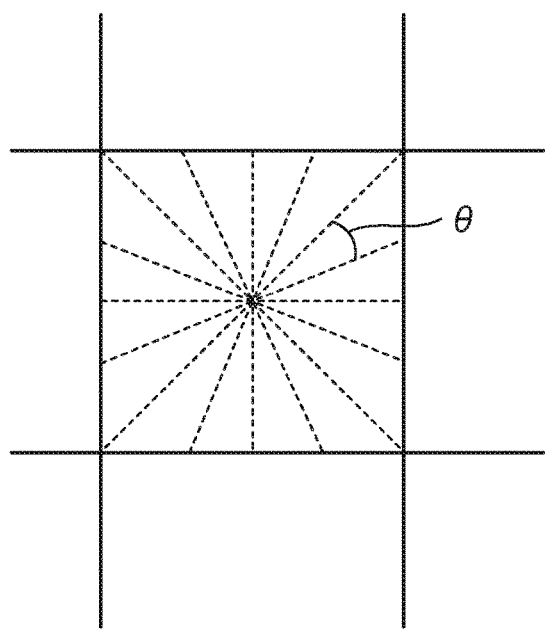
FIG. 11 is an enlarged view of one of the meshes illustrated in FIG. 10.

A scattering coefficient distribution of the measurement subject 2 is estimated by an inverse analysis arithmetic operation using the measured value in FIG. 9. FIG. 10 is a diagram illustrating that the measurement subject illustrated in FIG. 7 is divided into meshes. FIG. 11 is an enlarge view of one of the meshes illustrated in FIG. 10. As illustrated in FIG. 11, each of the meshes is further divided equally into 16 areas each with an angle θ (22.5°).

Figure 12:
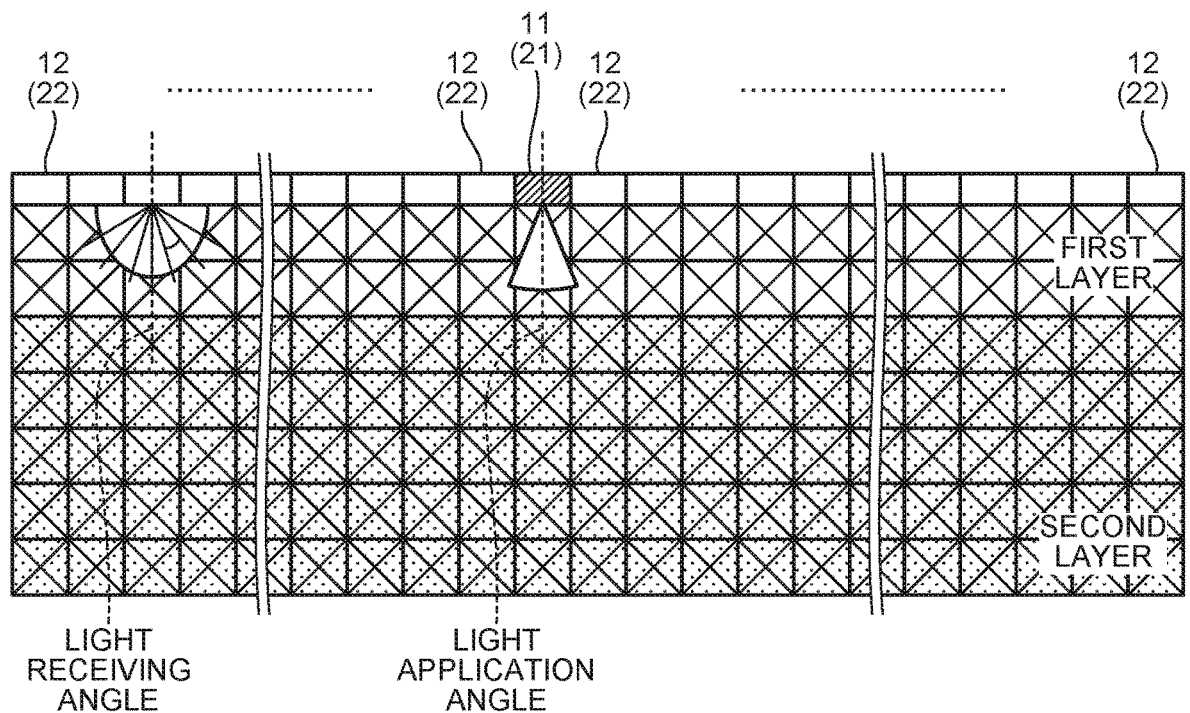
FIG. 12 is a diagram illustrating that an illuminator and a light receiver are arranged with respect to the measurement subject illustrated in FIG. 10.

FIG. 12 is a diagram illustrating that an illuminator and a light receiver are arranged with respect to the measurement subject illustrated in FIG. 10. As illustrated in FIG. 12, the illuminator 11 arranged at the center of the measurement subject 2 applies light to the surface of the measurement subject 2 orthogonally at a light application angle of 90°. The light applied from the illuminator 11 spreads at ±11.25°. The light receiver arranged over the surface of the measurement subject 2 receives light omnidirectionally at a light receiving angle from 90° at which light is orthogonal to the surface of the measurement subject 2 to ±90°.

In this state, a predicted value is estimated according to a known optical transport equation and a PCO (optimization using a partial differential equation as a constraint) algorithm (for example, refer to Academic Literature "Optical tomography as a PDE-constrained optimization problem" Inverse Problems 21 (2005) 1507-1530). Note that the method of estimating an optical physical property value distribution is not particularly limited. For example, an optical physical property value distribution may be estimated using a diffusion equation instead of the optical transport equation. For example, an optical physical property value distribution may be speculated on, numerical value calculation may be performed in advance using a light propagation model, the optical physical property value distribution and its corresponding calculated values of backscattering light may be put as a lookup table, and then an optical physical property value distribution may be estimated using an algorithm, such as simulated annealing, or the like.

Figure 13:
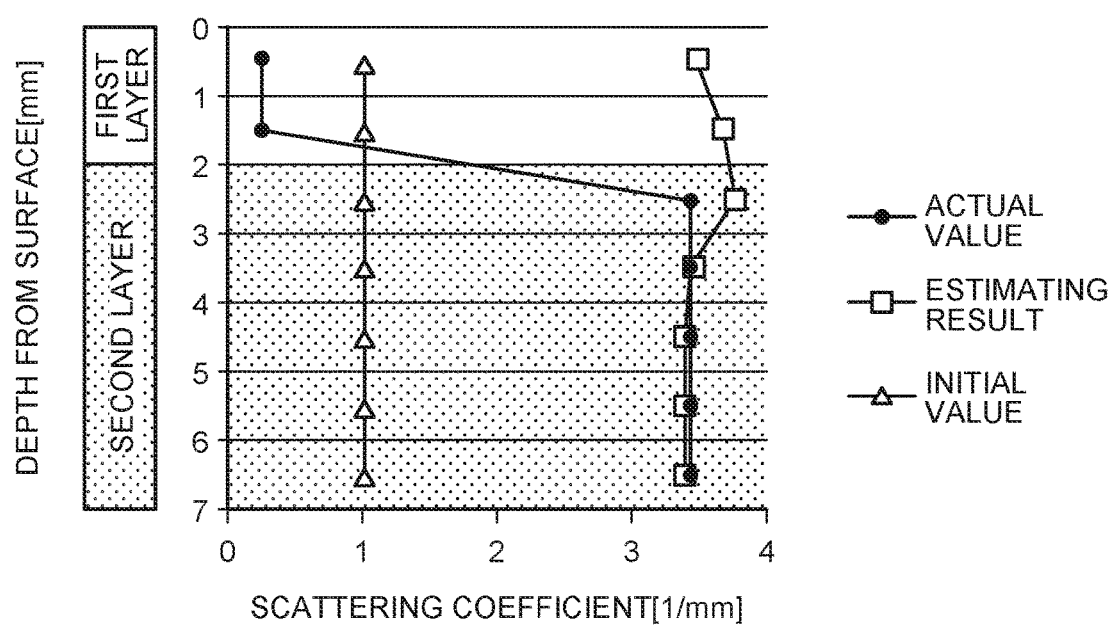
FIG. 13 is a graph representing a result of estimation by first estimating.

FIG. 13 is a graph representing a result of estimating by the first estimating. As represented in FIG. 13, for example, by performing an inverse analysis arithmetic operation speculating that the initial value of scattering coefficient is 1, a result of estimating a scattering coefficient is calculated. The result of estimating is approximately equal to an actual value in a deep layer (second layer).

Figure 14:
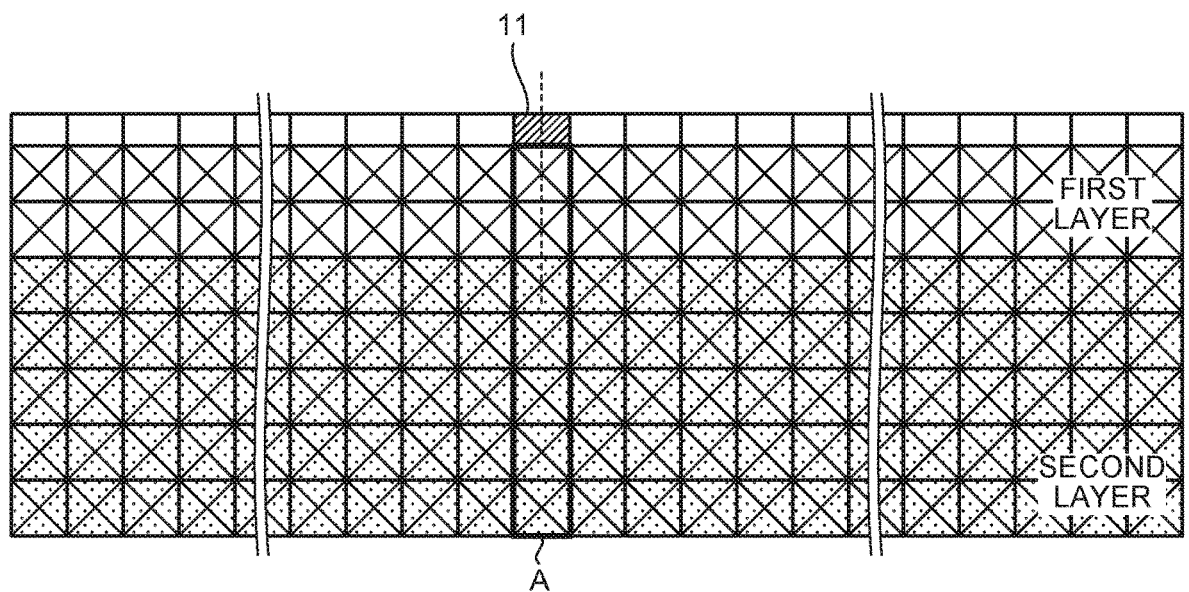
FIG. 14 is a diagram for explaining a method of setting an initial value by second estimating.
Figure 15:
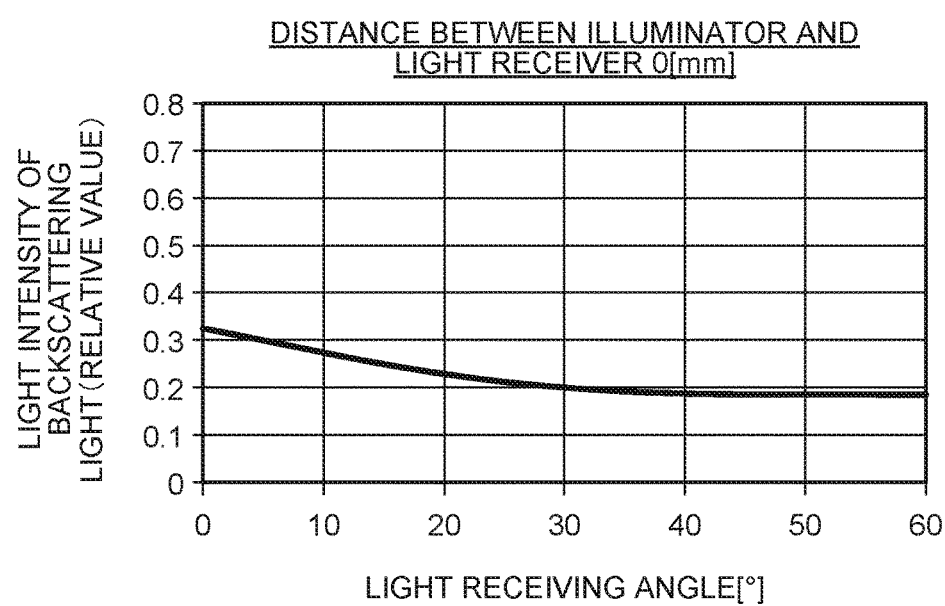
FIG. 15 is a graph representing a result of measuring by an angular distribution measuring unit.
Figure 16:
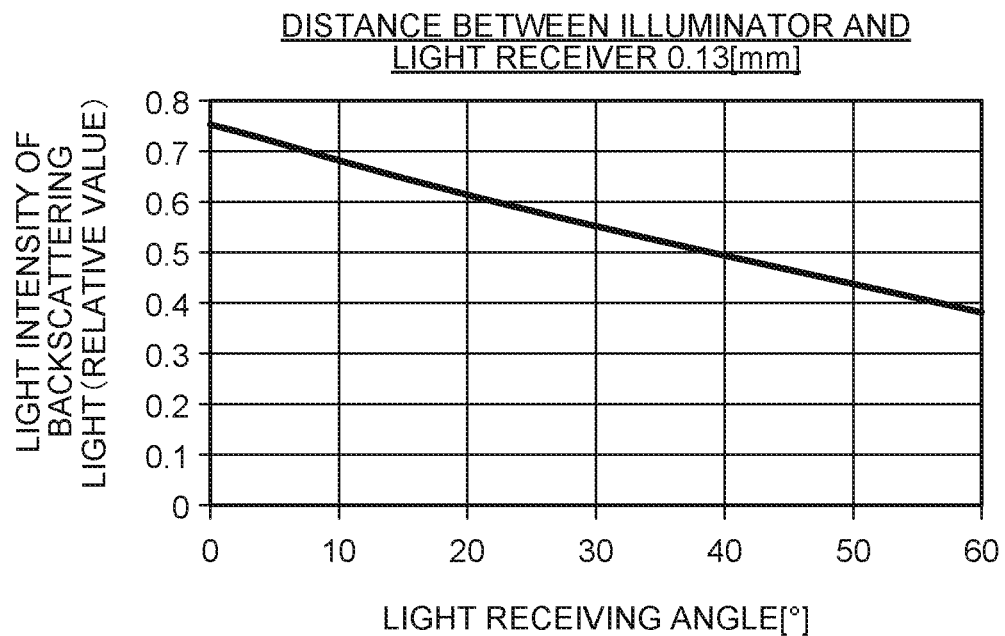
FIG. 16 is a graph representing another result of measuring by the angular distribution measuring unit.
Figure 17:
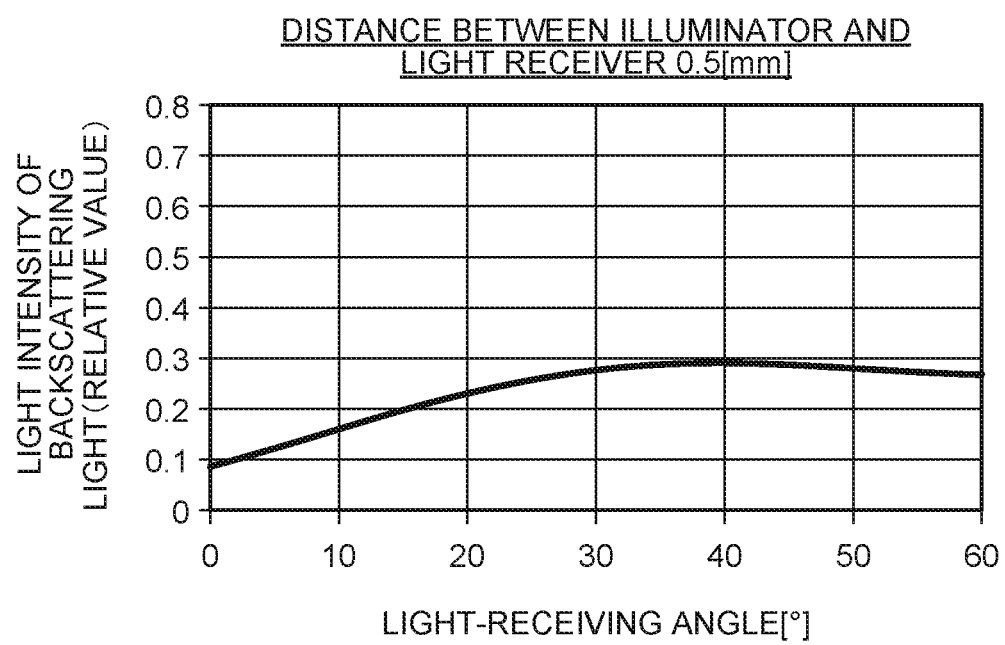
FIG. 17 is a diagram representing still another result of measuring by the angular distribution measuring unit.
Figure 18:
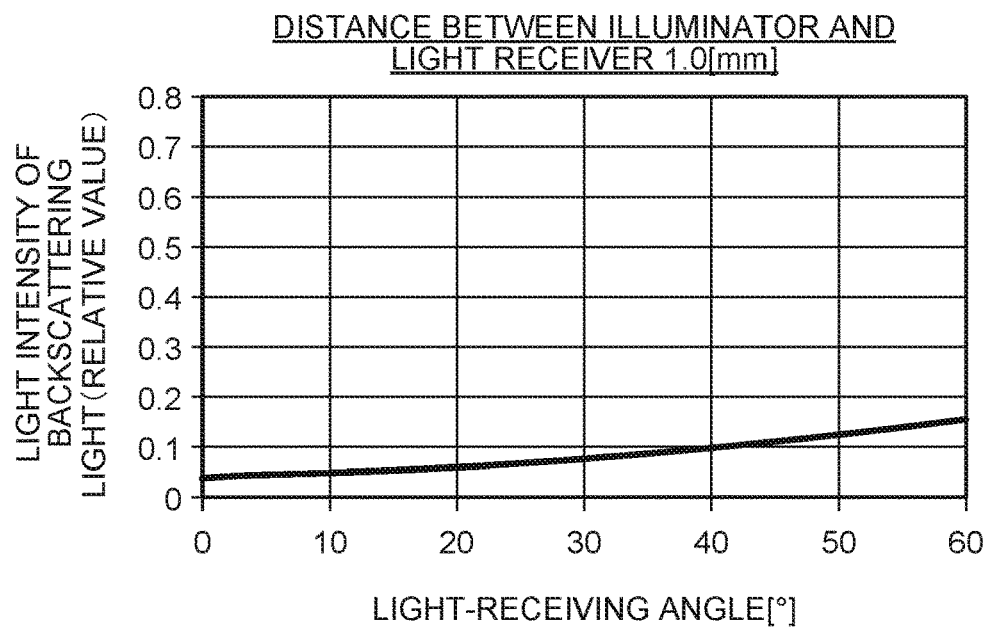
FIG. 18 is a graph representing still another result of measuring by the angular distribution measuring unit.

FIG. 14 is a diagram for explaining a method of setting an initial value at the second estimating. As illustrated in FIG. 14, the optical physical property values of the area excluding an area A are replaced with the result of estimation on the pillared area A right under the illuminator 11 and the result of estimation serves as an initial value of the second estimating. In other words, the second optical physical property value distribution is estimated using, as an initial value, resultant values obtained by replacing the optical physical property values of the whole area of the measurement subject 2 with the optical physical property values of the vertical area A in a direction orthogonal to the surface of the measurement subject 2 along light that is applied to the measurement subject 2 from among the first optical physical property value distribution. This is because the area A is an area that is right under the illuminator 11 and whose optical physical property values are estimated most accurately. As described above, in the second estimating, an inverse analysis arithmetic operation using part of the first optical physical property value distribution as an initial value may be performed. Furthermore, in this case, in the first estimating, the optical physical property values that are used for the second estimating may be calculated preferentially and calculating other optical physical property values in the first estimating may be performed in parallel with the second estimating. Depending on the internal structure of the measurement subject 2, it may be better to apply light from the illuminator 11 obliquely to the surface of the measurement subject 2. In this case, it suffices if the optical physical property values of the area excluding the pillared area along the light applied from the illuminator 11 be replaced with the result of estimation on the pillared area and the resultant values be used as an initial value of the second estimating. The illuminator 11 and the light receiver 12 may respectively include not a single light source and a single photodetector but a plurality of light sources and a plurality of photodetectors. In that case, it suffices if, based on results of estimation on a plurality of pillared areas along lights that are applied from the light sources, the optical physical property values in the area excluding the areas be replaced and the resultant values may serve as the initial value of the second estimating. Any one of the results of estimation on the pillared areas may be used as the initial value of the second estimating or values calculated by various known methods, such as values calculated by averaging or weighting the result of estimation on each of the pillared areas, may be used.

FIGS. 15 to 18 are graphs representing results of measuring by the angular distribution measuring unit. FIGS. 15 to 18 represent part of measured values obtained in a way that the distance 12 (refer to FIG. 2) between the illuminator 21 and the light receiver 22 is changed from 0 mm to 1.0 mm and, at each distance 12, the angle at which the light receiver 22 receives light is changed between 0° and 60°. As described, changing the distance 12 between the illuminator 21 and the light receiver 22 and the light receiving angle enables measurement of a light intensity angular distribution. Note that the light receiving angle is a center angle of light that is received by the light receiver 22 and the light receiver 22 receives light at a light receiving angle of ±11.25°.

Using measured values in FIGS. 15 to 18 and using the calculation model illustrated in FIG. 12, propagation of light in the measurement subject 2 is calculated and optical physical property values are calculated. The light receiver 22 that is arranged over the surface of the measurement subject 2 changes the light receiving angle from 0° to 60° and performs calculation.

Figure 19:
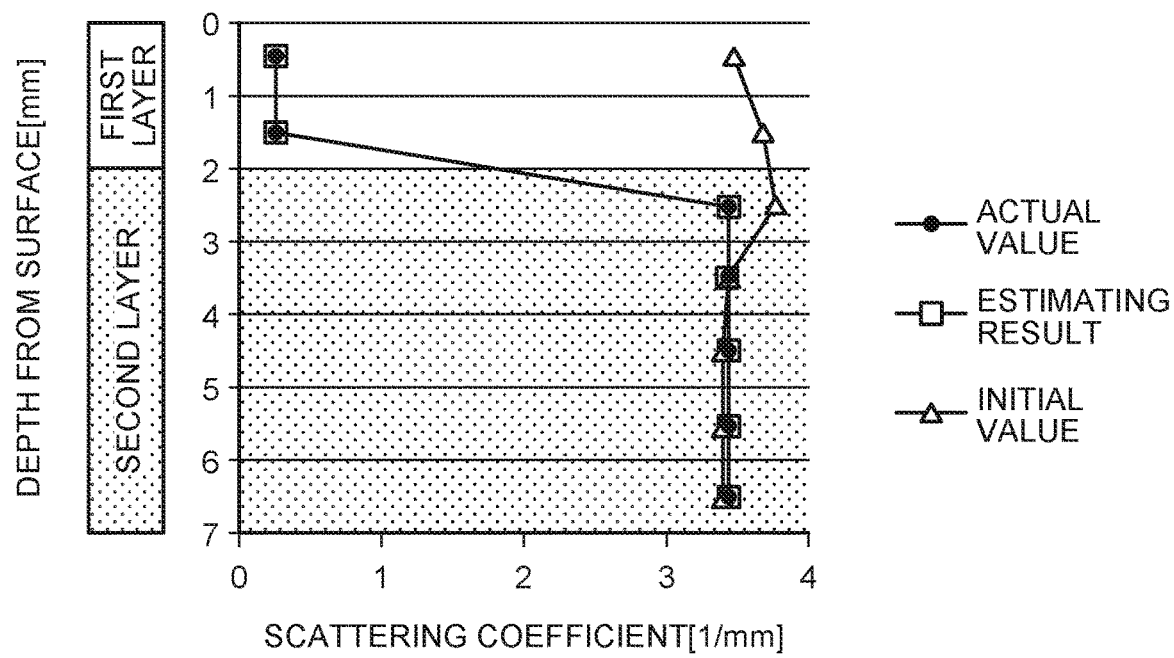
FIG. 19 is a graph representing a result of estimating by second estimating.

FIG. 19 is a graph representing a result of estimating by the second estimating. As illustrated in FIG. 19, estimating optical physical property values using the values of the first estimating as an initial value made it possible to obtain a result of estimating a scattering coefficient approximately equal to actual values.

Figure 20:
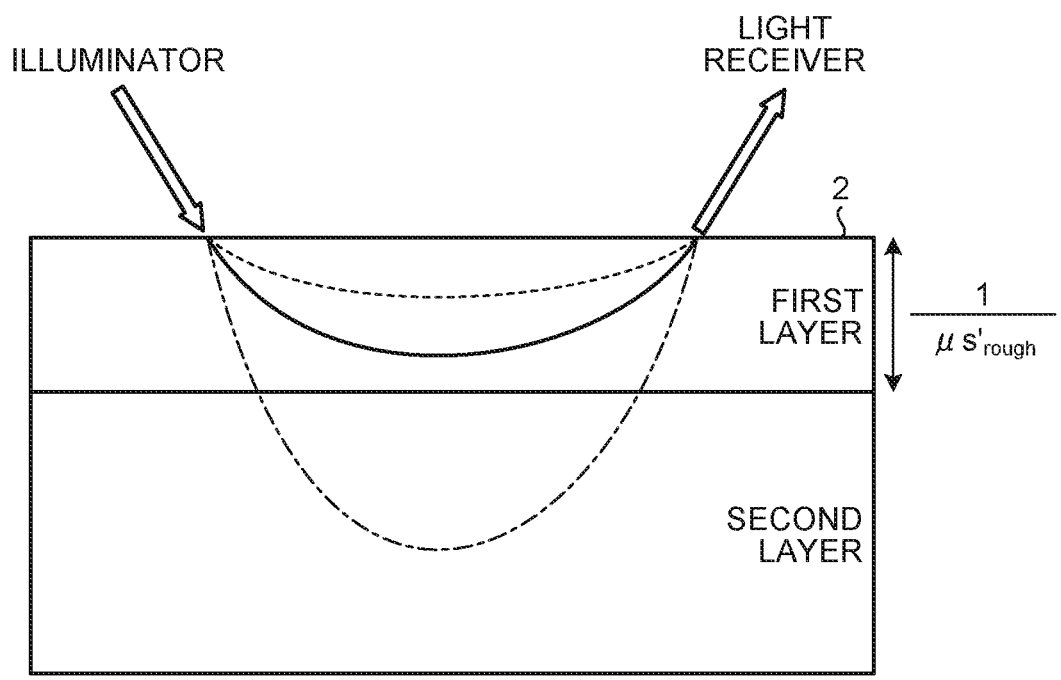
FIG. 20 is a diagram illustrating an exemplary method of estimating a thickness of a first layer.

When measuring a light intensity angular distribution, in the case where an approximate equivalent scattering coefficient $\mu s'_{rough}$ of the first layer of the measurement subject 2 is known from a literature, or the like, it suffices if the a light application angle and a light receiving angle be set such that light reaches the first layer sufficiently. FIG. 20 is a diagram illustrating an exemplary method of estimating a thickness of the first layer. As illustrated in FIG. 20, when the approximate equivalent scattering coefficient $\mu s'_{rough}$ of the first layer of the measurement subject 2 is known, the thickness of the first layer can be calculated by, for example, $1/\mu'_{rough}$. As described above, by predicting a depth of an area where the optical physical property values are small in the surface area of the measurement subject 2, determining an angle at which light is applied to the measurement subject 2 and an angle at which backscattering light from the measurement subject 2 is received according to the depth, and measuring second measured value at the determined angle, it is possible to estimate optical physical property values accurately in a short time. In other words, it is preferable that a second measured value be measured by a measuring method that is determined according to known optical physical property values (such as a scattering coefficient) representing a scattering intensity.

In the above-described embodiment, the configuration in which the TOF measuring unit 32 calculates a phase shift of intensity modulation between the light applied from the illuminator 11 and the light received by the light receiver 12 has been described; however, the configuration is not limited thereto. For example, when pulse light is applied from the illuminator 11 that is a pulse laser and the light receiver 12 that is a streak camera detects a time-resolved waveform of backscattering light in the measurement subject 2, the TOF measuring unit 32 may calculate, as TOF information, a time lag of light that is received by the light receiver 12 behind the pulse light that is applied from the illuminator.

According to the disclosure, it is possible to achieve a method of estimating an optical physical property value distribution, a computer-readable recording medium, and an optical physical property value distribution estimating apparatus that enable accurate estimation of an optical physical value distribution over a wide area from a shallow layer to a deep layer in living tissue.

The above and other features, advantages and technical and industrial significance of this disclosure will be better understood by reading the following detailed description of presently preferred embodiments of the disclosure, when considered in connection with the accompanying drawings.

What is claimed is:

1. A method of estimating an optical physical property value distribution that is performed by an optical physical property value distribution estimating apparatus configured to estimate an optical physical property value distribution in a measurement subject, the method comprising:
   first estimating including reading a first measured value obtained by measuring isotropic backscattering light of light that is applied to the measurement subject, from a storage and estimating a first optical physical property value distribution that is an optical physical property value distribution in the measurement subject, by an inverse analysis arithmetic operation; and
   second estimating including reading a second measured value obtained by measuring more anisotropic backscattering light of light that is applied to the measurement subject than the backscattering light corresponding to the first measured value, from a storage and estimating a second optical physical property value distribution that is an optical physical property value distribution in the measurement subject, by an inverse analysis arithmetic operation using at least part of the first optical physical property value distribution as an initial value.

2. The method according to claim 1, wherein the second optical physical property value distribution is an optical physical property value distribution of a layer shallower than a layer corresponding to the first optical physical property value distribution in the measurement subject.

3. The method according to claim 1, wherein the second estimating includes estimating the second optical physical property value distribution using, as an initial value, values obtained by replacing optical physical property values of a whole area of the measurement subject with optical physical property values of a vertical area that is an area in a direction orthogonal to a surface of the measurement subject along the light that is applied to the measurement subject, from among the first optical physical property value distribution.

4. The method according to claim 1, wherein
   the first measured value is values containing TOF information that is measured by applying pulse light or light whose intensity is modulated periodically to the measurement subject, and
   the first estimating includes estimating the first optical physical property value distribution based on the TOF information.

5. The method according to claim 1, wherein the second measured value is values each measured by setting, at an acute angle with respect to the surface of the measurement subject, at least any one of an angle at which light is applied to the measurement subject and an angle at which backscattering light from the measurement subject is received, and the second estimating includes estimating the second optical physical property value distribution based on a light intensity angular distribution of the second measured value.

6. The method according to claim 1, wherein the first measured value is values that are measured using at least any one of a photoacoustic phenomenon and a cross Nicol method.

7. The method according to claim 1, wherein the second measured value is values that are measured using at least any one of an OCT method and an open Nicol method.

8. The method according to claim 1, wherein the second measured value is values measured by a measurement method that is determined according to known optical physical property values representing a scattering intensity.

9. The method according to claim 8, further comprising
   predicting a depth of an area where the optical physical property values are small in a surface area of the measurement subject,
   determining the angle at which light is applied to the measurement subject and the angle at which backscattering light from the measurement subject is received according to the depth, and
   measuring the second measured value at the determined angles.

10. The method according to claim 9, wherein the depth is calculated by $1/\mu s'_{rough}$ using an approximate equivalent scattering coefficient $\mu s'_{rough}$ of the measurement subject.

11. A method of estimating an optical physical property value distribution that is performed by an optical physical property value distribution estimating apparatus configured to estimate an optical physical property value distribution in a measurement subject, the method comprising:
   first estimating including reading a first measured value obtained by measuring backscattering light of light that is applied to the measurement subject, from a storage and estimating a first optical physical property value distribution that is an optical physical property value distribution in a first area containing an area on which it is supposed that an optical energy loss in the measurement subject is large, by an inverse analysis arithmetic operation; and
   second estimating including reading a second measured value obtained by measuring backscattering light of light that is applied to the measurement subject, from a storage and estimating a second optical physical property value distribution that is an optical physical property value distribution in a second area on which it is supposed that a loss of optical energy is smaller than the optical energy loss in the first area in the measurement subject, by an inverse analysis arithmetic operation using at least part of the first optical physical property value distribution as an initial value.

12. A method of estimating an optical physical property value distribution that is performed by an optical physical property value distribution estimating apparatus configured to estimate an optical physical property value distribution in a measurement subject, the method comprising:
   first estimating including reading a first measured value obtained by measuring backscattering light of light that is applied to a first area in the measurement subject, from a storage and estimating a first optical physical property value distribution that is an optical physical property value distribution in the measurement subject, by an inverse analysis arithmetic operation; and
   second estimating including reading a second measured value obtained by measuring backscattering light of light that is applied to a second area contained in the first area from a storage and estimating a second optical physical property value distribution that is an optical physical property value distribution of a layer shallower than a layer corresponding to the first physical property value distribution in the measurement subject, by an inverse analysis arithmetic operation using at least part of the first optical physical property value distribution as an initial value.

13. A non-transitory computer-readable recording medium with an executable program stored thereon, the program causing an optical physical property value distribution estimating apparatus configured to estimate an optical physical property value distribution in a measurement subject to execute:

first estimating including reading a first measured value obtained by measuring isotropic backscattering light of light that is applied to the measurement subject, from a storage and estimating a first optical physical property value distribution that is an optical physical property value distribution in the measurement subject, by an inverse analysis arithmetic operation; and second estimating including reading a second measured value obtained by measuring more anisotropic backscattering light of light that is applied to the measurement subject than the backscattering light corresponding to the first measured value, from a storage and estimating a second optical physical property value distribution that is an optical physical property value distribution of a layer shallower than a layer corresponding to the first optical physical property value distribution in the measurement subject, by an inverse analysis arithmetic operation using at least part of the first optical physical property value distribution as an initial value.

14. An optical physical property value distribution estimating apparatus configured to estimate an optical physical property value distribution in a measurement subject, the apparatus comprising an inverse analysis arithmetic circuit configured to read a first measured value obtained by measuring isotropic backscattering light of light that is applied to the measurement subject, from a storage and estimate a first optical physical property value distribution that is an optical physical property value distribution in the measurement subject, by an inverse analysis arithmetic operation, and read a second measured value obtained by measuring more anisotropic backscattering light of light that is applied to the measurement subject than the backscattering light corresponding to the first measured value, from a storage and estimate a second optical physical property value distribution that is an optical physical property value distribution of a layer shallower than a layer corresponding to the first optical physical property value distribution in the measurement subject, by an inverse analysis arithmetic operation using at least part of the first optical physical property value distribution as an initial value.

* * * * *